United States Patent [19]

Iino et al.

[11] Patent Number: 5,709,853

[45] Date of Patent: Jan. 20, 1998

[54] METHOD OF TREATMENT OF ATOPIC DISEASE

[75] Inventors: Shiro Iino, Tokyo; Yoshiharu Kawashima, Kanagawa-ken, both of Japan

[73] Assignee: Toray Industries, Inc., Japan

[21] Appl. No.: 525,755

[22] PCT Filed: Jan. 28, 1994

[86] PCT No.: PCT/JP94/00124

§ 371 Date: Nov. 3, 1995

§ 102(e) Date: Nov. 3, 1995

[87] PCT Pub. No.: WO95/20395

PCT Pub. Date: Aug. 3, 1995

[51] Int. Cl.$^6$ .................................................. A61K 38/21
[52] U.S. Cl. ............................................................ 424/85.6
[58] Field of Search ............................................. 424/85.6

[56] References Cited

PUBLICATIONS

The Merck Index, 11Ed, No. 4892, Merck & Co., Inc., Rahway, N.J. 1989, p. 791.
Reinhold, Uwe, et al., "Systemic Interferon gamma treatment in severe atopic dermatitis," J. Am. Acad. Dermatol. 29(1), 58–63 (1993).
Pung, Yung-Hao, et al., "Use of interferons in atopic (IgE-mediated) diseases," Ann. Allergy 71, 234–38 (1993).
Johnson et al, *Scientific American*, 68, 73 (May 1994).

*Primary Examiner*—Jerome D. Goldberg
*Attorney, Agent, or Firm*—Austin R. Miller

[57] ABSTRACT

The present invention relates to pharmaceutical composition for atopic disease comprising interferon β as an active ingredient, because it significantly improved dermatic symptoms of atopic dermatitis, decreased the number of blood eosinocytes remarkably which is a main causative factor of allergic reactions, and exhibited a fast-acting and prolonged effect.

3 Claims, No Drawings

METHOD OF TREATMENT OF ATOPIC DISEASE

TECHNICAL FIELD

The present invention relates to a novel pharmaceutical composition for atopic disease.

BACKGROUND ART

Atopic diseases is a generic name for allergic diseases which are developed by exposing to extrinsic allergens individuals who have a family factor of being easily sensitized by such allergens. Patients having the factors of this disease easily exhibit severe hypersensitivities by alimentary antigens and inhalants. The patients also easily experience abnormalities in autonomic nerves, endocrines and immunological systems, by extrinsic invasions such as fever, coldness, humidity, injury, infection, or by intrinsic stress such as a mental strain. More specifically, atopic dermatitis, extrinsic bronchial asthma, urticaria, allergic rhinitis, allergic enterogastritis and the like are considered as atopic diseases.

As drug therapy for atopic disease, at present, antihistaminics, steroids, bronchodilators and others are employed as symptomatic therapies.

Among them, steroids are used mainly, however, they have some problems in clinical use. That is, they require a long-term administration to exhibit their effects, and further, they have local and systemic side effects. Thus, a useful drug has been desired which can substitute for or support steroids, and, furthermore, can be used as a causal treatment.

Recently, it has been found that atopic diseases are caused by immunological abnormalities, and that, especially, an acceleration of IgE production is a main factor of the disease. Therefore, immunomodulators for immunological abnormality, such as levamisole, transfer factors, thymopentin-pentapeptide, and cyclosporin have been applied. On the other hand, interferon $\gamma$ and interferon $\alpha$ have been known to possess strong immunomodulatory effects, and it was reported that they strongly inhibited production of IgE from lymphocytes (Pene J. et al., Proc. Nat. Acad. Sci. (USA), 1988; 85, 6880-4), production of interferon $\gamma$ was inhibited in local infiltrative lymphocytes associated with atopic dermatitis and asthma (J. Immunol., 1979; 123, 1788-94), and interferon $\gamma$ inhibited an enhancement of helper T2 lymphocytes (Gajewski TF et al., J. Immunol., 1988; 140, 4245-52). Thus, interferon $\gamma$ and interferon $\alpha$ have been used for treatment of atopic dermatitis and asthma, providing good results (Parkin JM et al., Br. Med. J., 1987; 294, 1185-6, Hanifin JM et al., J. Am. Acad. Dermatol., 1993; 28, 187-97, etc.). They have, however, not yet been applied to a practical use, because their results from clinical studies are not constant, therapeutic effects are not continuous, the disease will recur in a short time after the end of the administration, and some side effects are associated with them in the case of long-term administration.

As mentioned above, a pharmaceutical composition for atopic diseases up to now has not yet been provided, which has a fast-acting property and a prolonged action with less side effects. The object of the present invention is to provide a novel pharmaceutical composition for atopic diseases which is more effective and able to overcome the defects of conventional drugs.

DISCLOSURE OF THE INVENTION

The present invention relates to a pharmaceutical composition for atopic diseases comprising interferon $\beta$ as an active ingredient.

BEST MODE FOR CARRYING OUT THE INVENTION

Interferon $\beta$ in accordance with the present invention may be a natural type, a product from chemical synthesis, or a product obtained by gene recombinant technique, and also may be a polypeptide having the active site structure of the above three types of interferon $\beta$ therein. Natural interferon $\beta$ produced by human diploid fibroblasts are preferably used in the present invention.

Natural interferon $\beta$ may be obtained as follows. Interferon $\beta$ producing cells, which have been cultured on the surface of glass, plastic, or a microcarrier of DEAE-dextran, etc. receive an induction treatment with synthetic double-stranded RNA such as Poly I:C, followed by a super-induction treatment (such as a metabolic inhibition method combining cyclohexamide and actinomycin D, or an ultraviolet light radiation method). The cells are then cultured for 20 to 48 hr. in a medium which natural interferon $\beta$ is produced therein and recovered as a liquid comprising human interferon $\beta$.

In general, the concentration of interferon $\beta$ obtained by the method mentioned above is low, and the liquid includes many impurities from cells or additives. Therefore, it is necessary to concentrate and purify the interferon $\beta$ for medical use. Chromatography technique using insoluble carriers bonded to blue pigment and carriers bonded to metal chelate groups is preferable as concentration and purification method, although it is not restrictive. That is, a liquid including Crude interferon $\beta$ is contacted with insoluble carriers bonded to blue pigment, and the interferon $\beta$ is recovered as a solution by an eluant. The solution containing interferon $\beta$ is then contacted with carriers bonded to metal chelate groups such as zinc, and recovered by an eluant to obtained concentrated and purified interferon $\beta$.

Interferon $\beta$ of the present invention is useful as an agent for a group of diseases, such as atopic dermatitis, atopic asthma, urticaria, allergic rhinitis, allergic enterogastritis, comprising various symptoms induced by atopy, and is especially useful for atopic dermatitis and atopic asthma.

To use as a pharmaceutical composition for atopic diseases, interferon $\beta$ of the present invention may be orally or parenterally administrated as it is or in the form of a pharmaceutical composition mixed with known and pharmaceutically acceptable carriers, excipients, etc. Stabilizers may be also added to an atopic disease remedy of the present invention if required. Examples of those stabilizers are human serum albumin, polyol disclosed by Japan Patent Laid-Open No. 58-92619, and an organic acid buffer agent disclosed by Japan Patent Laid-Open No. 58-92621.

Various dosage forms may be employed, such as an injectable preparation, an oral preparation, a nasal preparation, a pulmonary preparation, a gastrointestinal mucosal preparation, an ointment, and an embrocation.

Although treatment doses are determined properly according to the object and method of the administration, symptoms, etc., the dose range of 100,000 to 10,000,000 unit/day, preferably 500,000 to 7,000,000 unit/day, is applied to a systemic administration, and one tenth to one thousandth of it is used for a local administration in general.

EXAMPLES

The present invention is illustrated in more detail by reference to the following examples.

Example 1

6,000,000 unit/day of human interferon $\beta$ (Feron, manufactured by Toray Industries, Inc. Japan) was administrated intravenously for six consecutive weeks to a patient with hepatitis C who was a 27-year-old male and suffered from atopic dermatitis. Although the patient's atopic dermatitis was a severe one and existed throughout his body, the redness caused by the disease disappeared one to two weeks after the beginning of the administration with a remarkable decrease in desquamation. The patient's itching was also improved greatly. This condition was maintained until two to three months after the conclusion of the administration.

The numbers of white blood cells and eosinocytes before and after the administration are shown in Table 1.

In the Table, WBC represents white blood cells and EOSINO represents eosinocytes. The number of eosinocytes which can be used as an activity index of allergic diseases increases before the administration, but decreases remarkably during the administration period.

Example 2

1,000,000 unit/day of natural human interferon $\beta$ (Feron, manufactured by Toray Industries, Inc.) was administrated intravenously for six consecutive weeks to a patient with hepatitis C who was a 57-year-old male and suffered from atopic dermatitis. One to two weeks after the beginning of the administration, those symptoms such as redness, desquamation, and itching were improved remarkably over the patient's entire body, and reached remission, maintaining this condition until two to three months after the conclusion of the administration.

The numbers of white blood cells and eosinocytes before and after the administration are shown in Table 1. The number of eosinocytes is low before the administration, and is maintained at low values during the administration period.

TABLE 1

CHANGE OF BLOOD EOSINOCYTES BY IFN ADMINISTRATION

| No. | Dose | Measurement time | −1 month | −1 week | Just before administration | 1 week | 2 week | 3 week |
|---|---|---|---|---|---|---|---|---|
| 1 | 6,000,000 IU/day | WBC[/mm$^3$] | 4800 | 4500 | 5000 | 2600 | 3000 | 2400 |
|   |   | EOSINO[%] | 7 | 7 | 5 | 1 | 0 | 2 |
|   |   | EOSINO[/mm$^3$] | 336 | 315 | 250 | 26 | 0 | 48 |
| 2 | 1,000,000 IU/day | WBC[/mm$^3$] | 4200 | 4000 | 4700 | 3400 | 3700 | 3700 |
|   |   | EOSINO[%] | 4 | 2 | 1 | 1 | 2 | 1 |
|   |   | EOSINO[/mm$^3$] | 168 | 80 | 47 | 34 | 74 | 37 |

| No. | Dose | Measurement time | 4 week | 5 week | Just after administration | +1 week | +2 week | +3 week |
|---|---|---|---|---|---|---|---|---|
| 1 | 6,000,000 IU/day | WBC[/mm$^3$] | 2400 | 2900 | 2500 | 4000 | 6500 | 4500 |
|   |   | EOSINO[%] | 0 | 1 | 3 | 5 | 6 | 2 |
|   |   | EOSINO[/mm$^3$] | 0 | 29 | 75 | 200 | 390 | 90 |
| 2 | 1,000,000 IU/day | WBC[/mm$^3$] | 3300 | 3900 | 4200 | 3900 | 4300 |   |
|   |   | EOSINO[%] | 6 | 6 | 4 | 4 | 1 |   |
|   |   | EOSINO[/mm$^3$] | 198 | 234 | 168 | 156 | 43 |   |

Industrial Applicability

Interferon $\beta$ is useful as a pharmaceutical composition for atopic diseases because it significantly improved dermatic symptoms of atopic dermatitis, decreased the number of blood eosinocytes remarkably which is a main causative factor of allergic reactions, and exhibited a fast-acting and prolonged effect.

What is claimed is:

1. A method of treating atopic disease comprising administering to a patient in need thereof an effective dose of interferon-$\beta$.

2. The method defined in claim 1 wherein said atopic disease is atopic dermatitis or atopic asthma.

3. A method of treating atopic disease comprising administering to a patient in need thereof an effective dose of a pharmaceutical composition containing a concentrated and purified interferon-$\beta$ combined with a pharmaceutically acceptable carrier.

* * * * *

UNITED STATES PATENT AND TRADEMARK OFFICE
CERTIFICATE OF CORRECTION

PATENT NO. : 5,709,853
DATED : January 20, 1998
INVENTOR(S) : Shiro Lino, Yoshiharu Kawashima It is certified that error appears in the above-indentified patent and that said Letters Patent is hereby corrected as shown below:

In column 2, line 33, please change "cheiate" to --chelate--.

Signed and Sealed this

Twenty-fourth Day of March, 1998

Attest:

BRUCE LEHMAN

*Attesting Officer*    *Commissioner of Patents and Trademarks*